(12) United States Patent
Wynn (10) Patent No.: US 8,829,059 B2
(45) Date of Patent: *Sep. 9, 2014

(54) PROCESSES FOR THE PRODUCTION OF METHANOL USING SWEEP-BASED MEMBRANE SEPARATION STEPS

(71) Applicant: Nicholas P. Wynn, Redwood City, CA (US)

(72) Inventor: Nicholas P. Wynn, Redwood City, CA (US)

(73) Assignee: Membrane Technology and Research, Inc., Newark, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/826,682

(22) Filed: Mar. 14, 2013

(65) Prior Publication Data
US 2014/0005285 A1    Jan. 2, 2014

Related U.S. Application Data

(60) Provisional application No. 61/665,071, filed on Jun. 27, 2012.

(51) Int. Cl.
C07C 27/10 (2006.01)
(52) U.S. Cl.
USPC .......................................................... 518/705
(58) Field of Classification Search
USPC .......................................................... 518/705
See application file for complete search history.

(56) References Cited

U.S. PATENT DOCUMENTS

| | | | |
|---|---|---|---|
| 1,569,775 A | 1/1926 | Mittasch et al. | |
| 4,963,165 A | 10/1990 | Blume et al. | |
| 5,034,126 A | 7/1991 | Reddy et al. | |
| 7,964,020 B2 | 6/2011 | Baker et al. | |
| 8,025,715 B2 | 9/2011 | Wijmans et al. | |
| 8,168,685 B2 | 5/2012 | Wynn et al. | |
| 8,177,885 B2 | 5/2012 | Wijmans et al. | |
| 8,246,718 B2 | 8/2012 | Wijmans et al. | |
| 2009/0277326 A1* | 11/2009 | Baker et al. | 95/50 |
| 2011/0260112 A1 | 10/2011 | Wijmans et al. | |
| 2013/0005840 A1* | 1/2013 | Wynn et al. | 518/705 |

OTHER PUBLICATIONS

Lin et al., "Materials selection guidelines for membranes that remove CO2 from gas mixtures" (J. Mol. Struct., 739, 57-75, 2005) and "Plastization-Enhanced Hydrogen Purification Using Polymeric Membranes" (Science, 311, 639-642, 2006).
K. O'Brien et al. "Fabrication and Scale-Up of PBI-based Membrane System for Pre-Combustion Capture of Carbon Dioxide" (DOE NETL Project Fact Sheet 2009).

(Continued)

*Primary Examiner* — Jafar Parsa
*Assistant Examiner* — Amy C Bonaparte
(74) *Attorney, Agent, or Firm* — T. Hott; J. Farrant (57) ABSTRACT

Disclosed herein are methanol production processes that include a sweep-based membrane separation step using a membrane that is selective to carbon dioxide over hydrogen. Using the processes of the invention, the efficiency of methanol production from syngas is increased by reducing the compression requirements of the process and/or improving the methanol product yield. In certain embodiments, a hydrogen-rich stream is generated; this hydrogen-rich stream can be sent for other uses. An additional benefit is that the processes of the invention may debottleneck existing methanol plants if more syngas or carbon dioxide is available, allowing for feed of imported carbon dioxide into the synthesis loop. This is a way of sequestering carbon dioxide.

18 Claims, 3 Drawing Sheets

(56) References Cited

OTHER PUBLICATIONS

B. T. Low et al. "Simultaneous Occurrence of Chemical Grafting, Cross-linking, and Etching on the Surface of Polyimide Membranes and Their Impact on H2/CO2 Separation" (Macromolecules, vol. 41, No. 4, pp. 1297-1309, 2008).

Lin, et al, "Plastization-Enhanced Hydrogen Purification Using Polymeric Membranes" (Science, 311, 639-642, 2006).

* cited by examiner

FIG. 1
(not in accordance with the invention)

PROCESSES FOR THE PRODUCTION OF METHANOL USING SWEEP-BASED MEMBRANE SEPARATION STEPS

FIELD OF THE INVENTION

The invention relates to methanol production processes that include a sweep-based membrane separation step using a membrane that is selective to carbon dioxide over hydrogen. Carbon dioxide recovered from the membrane separation step is recycled back to the methanol production process, resulting in sequestration of the carbon dioxide and production of additional methanol.

BACKGROUND OF THE INVENTION

Methanol, the simplest alcohol, with a chemical formula of $CH_3OH$, is a light, volatile, colorless, flammable liquid. A polar liquid at room temperature, methanol finds use as an antifreeze, solvent, fuel, and as a denaturant for ethanol. It is also used for producing biodiesel via a transesterification reaction.

The largest use of methanol, however, is in the manufacture of other chemicals. About forty percent of methanol is converted to formaldehyde, and from there into products as diverse as plastics, plywood, paints, explosives, and permanent-press textiles.

Methanol is also used on a limited basis as fuel for internal combustion engines. The use of methanol as a motor fuel received attention during the oil crises of the 1970's due to its availability, low cost, and environmental benefits. However, due to the rising cost of methanol and its corrosivity to rubber and many synthetic polymers used in the auto industry, by the late 1990's automakers had stopped building vehicles capable of operating on either methanol or gasoline ("flexible fuel vehicles"), switching their attention instead to ethanol-fueled vehicles. Even so, pure methanol is required as fuel by various auto, truck, and motorcycle racing organizations.

In 1923, German chemists Alwin Mittasch and Mathias Pier, working for BASF, developed a process for converting synthesis gas (a mixture of carbon monoxide, carbon dioxide, and hydrogen) into methanol. The process used a chromium and magnesium oxide catalyst and required extremely vigorous conditions—pressures ranging from 50 to 220 bar, and temperatures up to 450° C. A patent (U.S. Pat. No. 1,569,775) covering this process was issued on Jan. 12, 1926.

Modern methanol production has been made more efficient through the use of catalysts (typically copper) capable of operating at lower pressures. The modern low-pressure methanol (LPM) production process was developed by ICI in the late 1960s, with the technology now owned by Johnson Matthey (London), a leading licensor of methanol technology.

The production of synthesis gas ("syngas") via steam reforming of natural gas is the first step in many processes for methanol production. At low to moderate pressures and at high temperatures around 850° C., methane reacts with steam on a nickel catalyst to produce syngas according to the following reactions:

$$CH_4+H_2O \rightarrow CO+3H_2$$

$$CO+H_2O \rightarrow CO_2+H_2$$

This reaction, commonly referred to as "steam methane reforming" (SMR) is highly endothermic, and maintaining reaction temperature by external heating is a critical part of the process.

The syngas is then compressed and reacted on a second catalyst to produce methanol. Today, the most commonly used catalyst is a mixture of copper, zinc oxide, and alumina first used by ICI in 1966. At 50-100 bar and 250° C., it can catalyze the production of methanol from syngas with high selectivity:

$$CO+2H_2 \rightarrow CH_3OH$$

$$CO_2+3H_2 \rightarrow CH_3OH+H_2O$$

The production of syngas from methane produces 3 moles of hydrogen gas for every mole of carbon monoxide (and 4 moles of hydrogen per mole of carbon dioxide), while the methanol synthesis reaction consumes only 2 moles of hydrogen gas per mole of carbon monoxide (and 3 moles of hydrogen gas per mole of carbon dioxide). In both reaction pathways, one more mole of hydrogen is generated than is needed for methanol synthesis. This excess hydrogen occupies capacity in both the compressor train and the methanol reactor. As a result, the methanol production process is inefficient, resulting in unnecessary costs due to increased compressor power requirements and less than optimum methanol yields. Reactants are lost when excess hydrogen is purged from the synthesis loop and used as fuel for the reformer.

Figure 1:
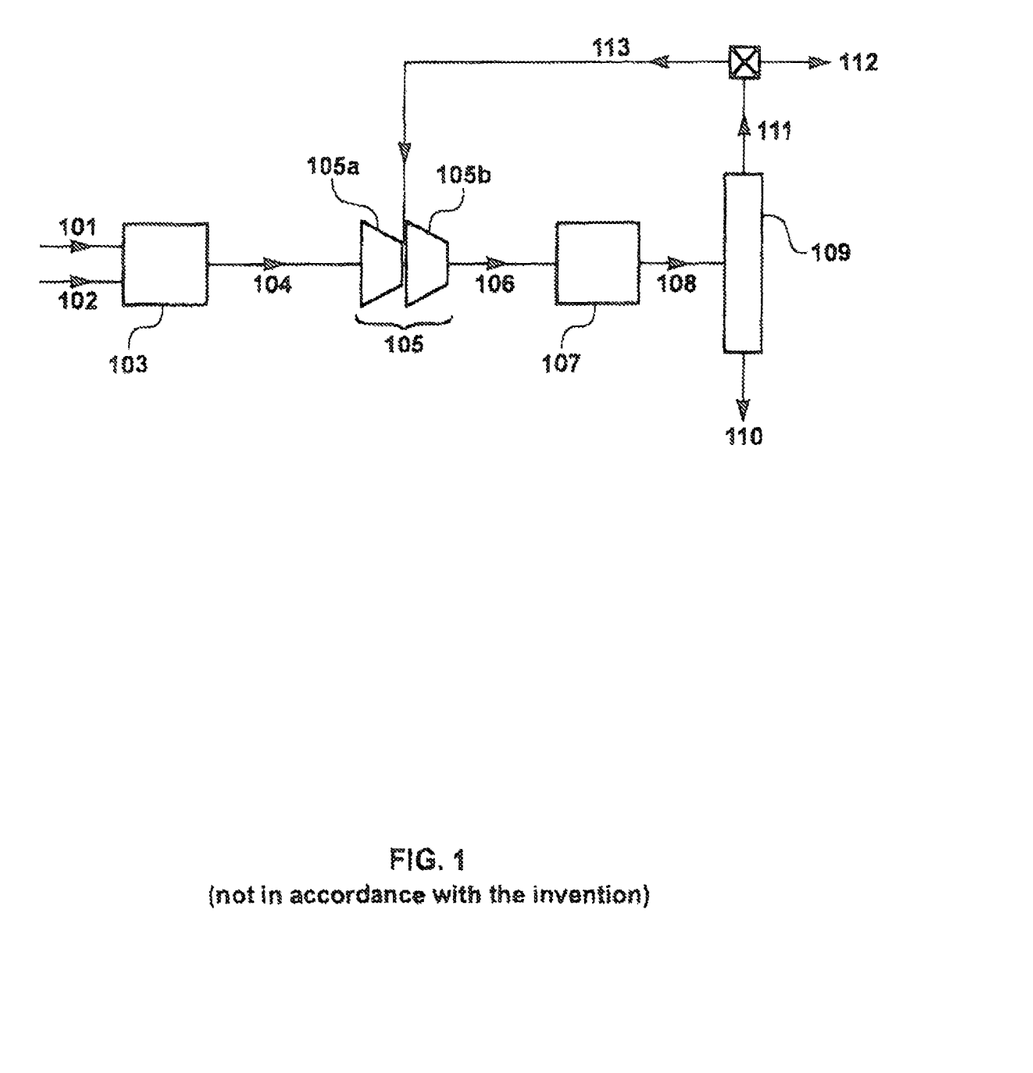
FIG. 1 is a schematic drawing of a conventional methanol production process (not in accordance with the invention).

FIG. 1 is a schematic showing a conventional process for methanol production. Feed streams of natural gas 101 and steam 102 are fed into reformer 103, resulting in the production of syngas stream 104. Syngas stream 104 is then passed to compression chain 105 (typically comprising at least make-up compressor 105a and recycle compressor 105b) to produce high-pressure gas stream 106. High-pressure stream 106 is then passed to methanol synthesis reactor 107 to produce reaction product stream 108, containing methanol and unreacted syngas. This stream 108 is then routed to condenser 109, from which condensed stream 110, containing methanol and water, drops out. Overhead stream 111, containing unreacted syngas and enriched in hydrogen and inerts (methane and possibly nitrogen), is then split into purge stream 112 and recycle stream 113, which is routed back to the recycle compressor 105b, where it is combined with fresh feed.

It would be desirable to provide an improved methanol production process that is more efficient, with reduced compressor power requirements and/or improved methanol product yield.

SUMMARY OF THE INVENTION

In commonly owned U.S. Pat. No. 8,168,685, issued May 1, 2012, we disclosed processes for the production of methanol from syngas which removed excess hydrogen from the syngas using hydrogen-selective membranes before the syngas reaches the methanol synthesis loop.

In a continuation-in-part of the aforementioned patent, copending U.S. application Ser. No. 13/446,667, filed Apr. 13, 2012 and published Jan. 1, 2013 as US Published Application 2013/0005840, we disclosed a methanol production process that includes at least two membrane separation steps after the methanol synthesis loop. This process uses a hydrogen-selective membrane followed by a carbon dioxide-selective membrane to improve the efficiency of methanol production from natural gas.

We have since discovered methanol synthesis loop production processes that include a carbon dioxide-selective sweep-based membrane separation step. The resulting carbon dioxide-enriched permeate stream from the sweep-based membrane separation step is compressed and then passed to the methanol synthesis reaction.

A basic process of the invention includes the following steps:

(a) providing a source of syngas, wherein the syngas has a composition parameter $R_1$, where $R_1 > 2$;

(b) performing a methanol synthesis reaction to react the syngas to produce methanol;

(c) performing a condensation step to recover methanol;

(d) withdrawing a purge stream from the condensation step to limit the concentration of inerts and excess hydrogen;

(e) withdrawing non-condensed methanol synthesis loop syngas from the condensation step;

(f) performing a sweep-based membrane separation step comprising, (i) providing a membrane having a feed side and a permeate side, where the membrane exhibits a selectivity to carbon dioxide over hydrogen, (ii) passing a carbon dioxide-containing gas across the feed side, (iii) passing at least a portion of the methanol synthesis loop syngas as a sweep stream across the permeate side, (iv) withdrawing from the feed side a carbon dioxide-depleted residue stream, and (v) withdrawing from the permeate side a carbon dioxide-enriched permeate stream;

(g) compressing the permeate stream; and (h) passing the compressed permeate stream to the methanol synthesis reaction.

Any membrane with suitable performance properties that exhibits a selectivity to carbon dioxide over hydrogen of at least 5 may be used in the sweep-based membrane separation step. Many polymeric materials, especially elastomeric materials, are very permeable to carbon dioxide. Preferred membranes for separating carbon dioxide from other gases often have a selective layer based on a polyether. The carbon dioxide permeance of the membrane is typically at least 200 gpu and, preferably, at least 400 gpu.

The membrane operating temperature is typically within the range of about 0° C. to about 80° C.; preferably, within the range of about 20° C. to about 60° C. The permeate side of the membrane is typically maintained at a pressure within the range of about 50 bar to about 100 bar, with the feed side typically maintained at a pressure within the range of about 3 bar to about 30 bar.

An alternative embodiment of the invention utilizes two membrane separation steps: a first membrane separation step utilizing a hydrogen-selective membrane, followed by a second, sweep-based membrane separation step that utilizes a carbon dioxide-selective membrane. The first membrane separation step generates a carbon dioxide-containing residue stream from methanol synthesis loop purge gas. This carbon dioxide-enriched residue stream is then passed across the feed side of a carbon dioxide-selective membrane, and methanol synthesis loop syngas is passed as a sweep stream across the permeate side of the carbon dioxide-selective membrane. The resulting carbon dioxide-enriched permeate stream is compressed and returned to the methanol synthesis reaction.

This two-membrane separation step embodiment includes the following basic steps:

(a) providing a source of syngas, wherein the syngas has a composition parameter $R_1$, where $R_1 > 2$;

(b) performing a methanol synthesis reaction to react the syngas to produce methanol;

(c) performing a condensation step to recover methanol;

(d) withdrawing a purge stream of composition parameter $R_3$ from the condensation step to limit the concentration of inerts and excess hydrogen;

(e) withdrawing non-condensed methanol synthesis loop syngas from the condensation step;

(f) performing a first membrane separation step comprising, (i) providing a first membrane having a first feed side and a first permeate side, where the first membrane exhibits a selectivity to hydrogen over carbon dioxide and carbon monoxide, (ii) passing at least a portion of the purge stream across the first feed side, (iii) withdrawing from the first permeate side a hydrogen-enriched first permeate stream, wherein the first permeate stream has a composition parameter $R_4$, where $R_4 > R_3$, and (iv) withdrawing from the first feed side a hydrogen-depleted first residue stream;

(g) performing a second, sweep-based membrane separation step comprising, (i) providing a second membrane having a second feed side and a second permeate side, where the second membrane is selective for carbon dioxide over hydrogen and methane, (ii) passing at least a portion of the first residue stream across the second feed side, (iii) passing at least a portion of the methanol synthesis loop syngas as a sweep stream across the second permeate side, (iv) withdrawing from the second feed side a carbon dioxide-depleted second residue stream;

(v) withdrawing from the second permeate side a carbon dioxide-enriched second permeate stream, wherein the second permeate stream has a composition parameter $R_5$, where $R_5 < R_3$;

(h) compressing the second permeate stream; and (i) passing the compressed second permeate stream to the methanol synthesis reaction.

Any membrane that exhibits a selectivity to hydrogen over carbon dioxide of at least about 5, preferably, at least about 10, and to hydrogen over carbon monoxide of at least about 20, may be used in the first membrane separation step. The hydrogen permeance of the first membrane is typically at least 100 gpu and, preferably, at least 200 gpu.

Preferred first membrane materials include polymers, such as polyimides, polyamides, polyurethanes, polyureas, polybenzimidazoles, and polybenzoxazoles; metals, such as palladium; zeolites; and, carbon, by way of example and not by way of limitation.

The first membrane operating temperature is typically within the range of about 50° C. to about 150° C.; preferably, within the range of about 100° C. to about 150° C. The feed side of the first membrane is typically maintained at a pressure within the range of about 45 bar to about 100 bar, with the permeate side typically maintained at a pressure within the range of about 2 bar to about 10 bar.

Any membrane that exhibits a selectivity to carbon dioxide over hydrogen of at least about 5, and over methane of at least about 10, may be used in the second, sweep-based membrane separation step. The carbon dioxide permeance of the second membrane is typically at least 200 gpu and, preferably, at least 400 gpu. Membrane materials are as discussed above with respect to the first embodiment of the invention.

The second membrane operating temperature is typically within the range of about 50° C. to about 150° C.; preferably, within the range of about 100° C. to about 150° C. The permeate side of the second membrane is typically maintained at a pressure within the range of about 50 bar to about 100 bar, with the feed side typically maintained at a pressure within the range of about 3 bar to about 10 bar.

By practicing the process of the invention, existing methanol plants can be made more efficient by recovering carbon dioxide and recycling it to the methanol synthesis reaction. This results in additional methanol production and is also a way of sequestering carbon dioxide, thereby preventing its release to the environment. In addition, embodiments of the invention generate a hydrogen-rich stream from the first membrane separation step. This hydrogen-rich stream can be used for other purposes.

DETAILED DESCRIPTION OF THE INVENTION

The terms "natural gas" and "methane" are used interchangeably herein.

Gas percentages given herein are by volume unless stated otherwise.

Pressures as given herein are in bar absolute unless stated otherwise.

For any gas stream herein, the composition may be expressed in terms of a composition parameter, R, where:

$$R = \frac{\text{(molar flow of } H_2 - \text{molar flow of } CO_2)}{\text{(molar flow of } CO + \text{molar flow of } CO_2)},$$

Specific composition parameters are referred to herein as $R_1$, $R_2$, $R_3$, $R_4$, and $R_5$.

Figure 2:
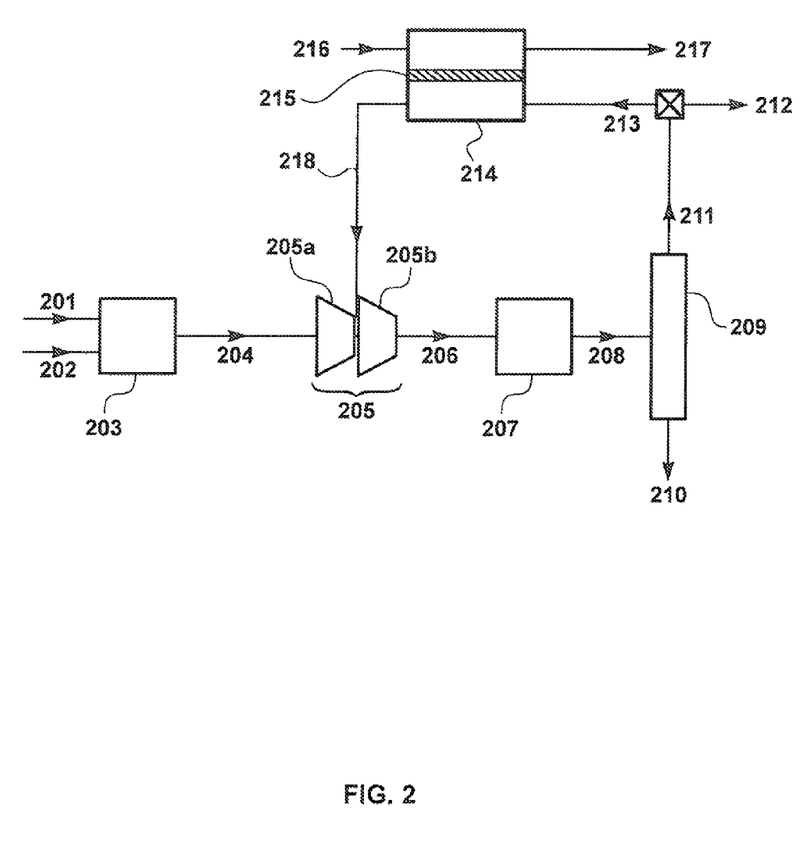
FIG. 2 is a schematic drawing of a basic embodiment process of the invention for a methanol synthesis loop production process that uses a sweep-based, carbon dioxide-selective membrane separation step to treat methanol synthesis loop syngas.

A schematic drawing of a basic embodiment process of the invention for methanol production is shown in FIG. 2. It will be appreciated by those of skill in the art that this, like FIG. 1, is a very simple block diagram, intended to make clear the key unit operations of the process of the invention, and that an actual process train will usually include many additional steps of a standard type, such as heating, chilling, compressing, condensing, pumping, various types of separation and/or fractionation, as well as monitoring of pressures, temperatures, flows, and the like. It will also be appreciated by those of skill in the art that the details of the unit operations may differ from product to product.

Referring to the figure, feed streams of natural gas, 201, and steam, 202, are fed into, for example, a steam reformer, 203, resulting in the production of syngas, 204. Although FIG. 2 illustrates an example in which syngas is produced using a steam methane reforming process, any source of syngas can be used to provide syngas for use in the process of the invention.

The invention is particularly designed for syngas sources having an excess of hydrogen for methanol production. Expressed quantitatively, the invention is particularly directed to the manufacture of methanol from syngas having a composition parameter, $R_1$, that is greater than 2; that is, $R=R_1>2$.

Syngas stream, 204, is then passed to a compressor train, 205 (typically comprising at least a make-up compressor, 205a, and a recycle compressor, 205b) to produce a high-pressure gas stream, 206. High-pressure stream 206 is then passed to a methanol synthesis reactor, 207, to produce a reaction product stream, 208, containing methanol and unreacted syngas.

Methanol synthesis reactors are known in the art and typically rely on a catalyst bed to catalyze the reaction of carbon oxides and hydrogen to produce methanol. As discussed in the Background of the Invention, the most common catalyst in use today is a mixture of copper, zinc oxide, and alumina first used by ICI in 1966. At 50-100 bar and 250° C., it can catalyze the production of methanol from carbon oxides and hydrogen with high selectivity.

Reaction product stream 208 is then routed to a condenser, 209, from which a condensed stream, 210, containing methanol and water, drops out. An overhead stream, 211, containing unreacted syngas and enriched in hydrogen and inerts (methane and possibly nitrogen), is withdrawn. To limit the concentration of inerts and excess hydrogen in the methanol synthesis loop, a portion of overhead stream 211 is withdrawn as a purge stream, 212.

In accordance with the present invention, at least a portion of overhead stream 211 is passed as methanol synthesis loop syngas, 213, to a membrane unit, 214, that includes membranes, 215, that are selective for carbon dioxide over hydrogen, methane, and nitrogen.

In particular, the membranes 215 typically have a selectivity for carbon dioxide over hydrogen of at least about 5; over methane of at least about 10; and, over nitrogen of at least about 20. The carbon dioxide permeance of the membrane is typically at least 200 gpu and, preferably, at least 400 gpu.

Any membrane with suitable performance properties may be used in the membrane separation step. Many polymeric materials, especially elastomeric materials, are very permeable to carbon dioxide. Such polymeric materials are described, for example, in two publications by Lin et al., "Materials selection guidelines for membranes that remove $CO_2$ from gas mixtures" (*J. Mol. Struct.*, 739, 57-75, 2005) and "Plastization-Enhanced Hydrogen Purification Using Polymeric Membranes" (*Science*, 311, 639-642, 2006).

Preferred membranes for separating carbon dioxide from other gases often have a selective layer based on a polyether. Not many membranes are known to have high carbon dioxide/hydrogen selectivity. A representative preferred material for the selective layer is Pebax®, a polyamide-polyether block copolymer material described in detail in U.S. Pat. No. 4,963, 165. We have found that membranes using Pebax® as the selective polymer can maintain a selectivity of 9, 10, or greater under process conditions.

The membrane may take the form of a homogeneous film, an integral asymmetric membrane, a multilayer composite membrane, a membrane incorporating a gel or liquid layer or particulates, or any other form known in the art.

The membranes may be manufactured as flat sheets or as fibers and housed in any convenient module form, including spiral-wound modules, plate-and-frame modules, and potted hollow-fiber modules. The making of all these types of membranes and modules is well-known in the art.

Flat-sheet membranes in spiral-wound modules is the most preferred choice for the membrane/module configuration. A number of designs that enable spiral-wound modules to be used in counterflow mode, with or without sweep on the permeate side, have been devised. A representative example is described in U.S. Pat. No. 5,034,126, to Dow Chemical.

Membrane unit 214 may contain a single membrane module or bank of membrane modules or an array of modules. A single unit or stage containing one or a bank of membrane modules is adequate for many applications. If the residue stream requires further carbon dioxide removal, it may be passed to a second bank of membrane modules for a second processing step. Such multi-stage or multi-step processes, and variants thereof, will be familiar to those of skill in the art, who will appreciate that the membrane separation step may be configured in many possible ways, including single-stage, multistage, multistep, or more complicated arrays of two or more units, in serial or cascade arrangements.

The membrane operating temperature is typically within the range of about 0° C. to about 80° C.; preferably, within the range of about 20° C. to about 60° C. The permeate side of the membrane is typically maintained at a pressure within the range of about 50 bar to about 100 bar, with the feed side typically maintained at a pressure within the range of about 3 bar to about 30 bar.

Returning to FIG. 2, methanol synthesis loop syngas 213 flows as a sweep gas across the permeate side of the membranes, and a carbon dioxide-containing gas, 216, flows across the feed side. The carbon dioxide may be imported from a local external source. For example, and not by way of limitation, the carbon dioxide may come from a chemical process such as ethylene oxide production.

Alternatively, the carbon dioxide may be imported from treated combustion exhaust gases generated by a coal-fired or natural gas-fired power plant, as described, for example, in commonly owned U.S. Pat. Nos. 7,964,020, 8,025,715, 8,177,885 and 8,246,718, and copending U.S. application Ser. No. 13/123,364, which published as US 2011/0260112 on Oct. 27, 2011. This is a way of sequestering power plant-generated carbon dioxide.

It is highly preferred that the feed gas flow direction and the sweep gas flow direction are substantially counter-current or, less preferred, cross-current, to each other.

In the process of the invention, the pressure of the carbon dioxide-containing feed gas is lower than the pressure of the methanol synthesis loop syngas. However, the pressure of the carbon dioxide-containing feed gas must be high enough to produce a carbon dioxide partial pressure higher than the carbon dioxide partial pressure in the methanol synthesis loop syngas. Feed gas at high carbon dioxide concentration may be used at lower pressures than feed gas at low carbon dioxide concentration. Because the partial pressure of carbon dioxide is higher on the feed side of the membrane, the carbon dioxide preferentially permeates to the permeate side of the membrane 215; a carbon dioxide-depleted residue stream, 217, is withdrawn from the feed side of membrane separation unit 214.

A carbon dioxide-enriched sweep permeate stream, 218, is withdrawn from membrane unit 214, and then returned to the methanol synthesis reaction, preferably to the suction side of the recycle compressor 205b. Because permeate stream 218 is carbon dioxide-enriched, returning it to the methanol synthesis reaction results in additional methanol production.

Figure 3:
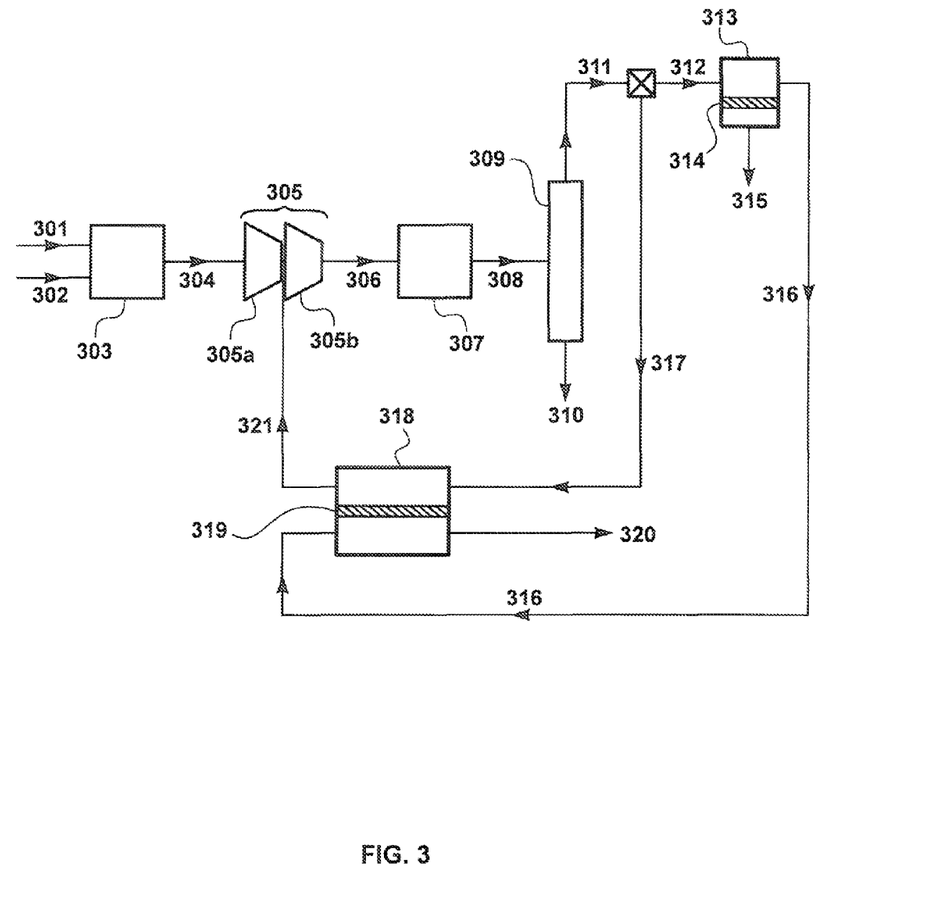
FIG. 3 is a schematic drawing of an alternative embodiment process of the invention for a methanol synthesis loop production process that uses a hydrogen-selective membrane separation step, followed by a sweep-based, carbon dioxide-selective membrane separation step, to treat methanol synthesis loop syngas.

In an alternative embodiment of the invention, a hydrogen-selective membrane is used to treat a purge stream from the methanol production process. Removing hydrogen from this stream generates a carbon dioxide-containing first residue stream at high pressure and adequate carbon dioxide concentration from a readily available source. In a second membrane separation step, this first residue stream is passed across the feed side of a carbon dioxide-selective membrane; at least a portion of the methanol synthesis loop syngas is passed as a sweep gas across the permeate side. The carbon dioxide-enriched permeate stream from this second membrane separation step is compressed and passed to the methanol synthesis reaction. A basic process schematic for this embodiment is shown in FIG. 3.

Referring to the figure, feed streams of natural gas, 301, and steam, 302, are fed into, for example, a steam reformer, 303, resulting in the production of syngas, 304. Although FIG. 3 illustrates another example in which syngas is produced using a steam methane reforming process, any source of syngas can be used to provide syngas for use in the process of the invention.

Syngas stream 304 is then passed to a compressor train, 305 (typically comprising at least a make-up compressor, 305a, and a recycle compressor, 305b) to produce a high-pressure gas stream, 306. High-pressure stream 306 is then passed to a methanol synthesis reactor, 307, to produce a reaction product stream, 308, containing methanol and unreacted syngas.

Reaction product stream 308 is then routed to a condenser, 309, from which a condensed stream, 310, containing methanol and water, drops out. An overhead stream, 311, is withdrawn. A portion of overhead stream 311 is withdrawn as a purge stream, 312, containing unreacted syngas and enriched in hydrogen and inerts (methane and possibly nitrogen). Purge stream 312 has a composition parameter $R_3$.

In accordance with this embodiment of the invention, at least a portion of purge stream 312 is sent as a feed stream for treatment in a first membrane separation unit, 313, that includes membranes, 314 that are selective for hydrogen over carbon dioxide and carbon monoxide. Preferably, membranes 314 exhibit a selectivity for hydrogen over carbon dioxide of at least about 5; preferably, at least about 10; more preferably, at least about 15. In addition, the membranes 314 should exhibit a selectivity for hydrogen over carbon monoxide of at least about 20. Hydrogen permeance of the first membrane is typically at least 100 gpu and, preferably, at least 200 gpu.

Any membrane with suitable performance properties may be used in the first membrane separation step. Examples of such membranes include the polybenzimidazole (PBI) based membranes taught by K. O'Brien et al. in "Fabrication and Scale-Up of PBI-based Membrane System for Pre-Combustion Capture of Carbon Dioxide" (DOE NETL Project Fact Sheet 2009) and polyimide-based membranes taught by B. T. Low et al. in "Simultaneous Occurrence of Chemical Grafting, Cross-linking, and Etching on the Surface of Polyimide Membranes and Their Impact on $H_2/CO_2$ Separation" (*Macromolecules*, Vol. 41, No. 4, pp. 1297-1309, 2008).

Preferred first membrane materials include polymers, such as polyimides, polyamides, polyurethanes, polyureas, polybenzimidazoles, and polybenzoxazoles; metals, such as palladium; zeolites; and carbon, by way of example and not by way of limitation.

Membrane modules are as discussed above with respect to the first invention embodiment.

The first membrane operating temperature is typically within the range of about 50° C. to about 150° C.; preferably, within the range of about 100° C. to about 150° C. The feed side of the first membrane is typically maintained at a pressure within the range of about 45 bar to about 100 bar, with the permeate side typically maintained at a pressure within the range of about 2 bar to about 10 bar.

Referring back to FIG. 3, stream 312 is passed across the feed side of the first membrane 314. A permeate stream, 315, is withdrawn from the permeate side. Permeate stream 315 is enriched in hydrogen as compared with stream 312, and has a composition parameter $R_4$, where $R_4>R_3$. This hydrogen-rich stream 315 can be used for whatever purpose is desired. It may, for example, be used as reformer fuel gas, or used as a source of hydrogen for another process, such as ammonia production.

A hydrogen-depleted first residue stream, 316, is withdrawn from the feed side of first membrane unit 313. At least a portion of first residue stream 316 is then routed as a feed stream to a second, sweep-based membrane separation unit, 318. Second membrane separation unit 318 includes membranes, 319, that are selective for carbon dioxide over hydrogen, methane, and nitrogen.

In particular, the membranes in second, sweep-based membrane unit 318 typically have a selectivity for carbon dioxide over hydrogen of at least about 5; over methane of at least about 10; and, over nitrogen of at least about 20. Carbon dioxide permeance of the second membrane is typically at least 200 gpu and, preferably, at least 400 gpu.

Any membrane with suitable performance properties may be used in the second, sweep-based membrane separation step. Carbon dioxide-selective membranes and membrane modules are as discussed above with respect to the process invention embodiment shown in FIG. 2.

The second membrane operating temperature is typically within the range of about 50 EC to about 150 EC; preferably, within the range of about 100° C. to about 150° C. The permeate side of the second membrane is typically maintained at a pressure within the range of about 50 bar to about 100 bar, with the feed side typically maintained at a pressure within the range of about 3 bar to about 10 bar.

Returning to FIG. 3, a portion of overhead stream 311 is withdrawn as methanol synthesis loop syngas, 317. This stream flows as a sweep stream across the permeate side of the second membrane 319, and first membrane residue stream 316 flows across the feed side, as discussed above.

As discussed above with respect to the process embodiment shown in FIG. 2, it is highly preferred that the feed gas flow direction and the sweep gas flow direction are substantially counter-current or, less preferred, cross-current, to each other.

The pressure of the carbon dioxide-containing first residue stream is lower than the pressure of the methanol synthesis loop syngas. However, the pressure of the carbon dioxide-containing feed gas to the sweep-based membrane separation step must be high enough to produce a carbon dioxide partial pressure higher than the carbon dioxide partial pressure in the methanol synthesis loop syngas. Feed gas at high carbon dioxide concentration may be used at lower pressures than feed gas at low carbon dioxide concentration. Because the partial pressure of carbon dioxide is higher on the feed side of the membrane, the carbon dioxide preferentially permeates to the permeate side of the membrane 319. A carbon dioxide-depleted residue stream, 320, is withdrawn from the feed side of second membrane separation unit 318. This stream typically contains methane and can be sent for use as fuel gas or for any other desired purpose.

A carbon dioxide-enriched second sweep/permeate stream, 321, is withdrawn from second membrane unit 318, and then returned to the methanol synthesis reaction, preferably to the suction side of the recycle compressor 305b. Second permeate stream 321 has a composition parameter $R_5$, where $R_5<R_3$. Because permeate stream 321 is carbon dioxide-enriched, returning it to the methanol synthesis reaction results in additional methanol production.

I claim:

1. A methanol synthesis loop production process comprising the following steps:
    (a) providing a source of syngas, wherein the syngas has a composition parameter $R_1$, where $R_1>2$;
    (b) performing a methanol synthesis reaction to react the syngas to produce methanol;
    (c) performing a condensation step to recover methanol;
    (d) withdrawing a purge stream from the condensation step to limit the concentration of inerts and excess hydrogen;
    (e) withdrawing non-condensed methanol synthesis loop syngas from the condensation step;
    (f) performing a sweep-based membrane separation step comprising,
        (i) providing a membrane having a feed side and a permeate side, where the membrane exhibits a selectivity to carbon dioxide over hydrogen,
        (ii) passing a carbon dioxide-containing gas across the feed side,
        (iii) passing at least a portion of the methanol synthesis loop syngas as a sweep stream across the permeate side,
        (iv) withdrawing from the feed side a carbon dioxide-depleted residue stream,
        (v) withdrawing from the permeate side a carbon dioxide-enriched permeate stream;
    (g) compressing the permeate stream; and
    (h) passing the compressed permeate stream to the methanol synthesis reaction.

2. The process of claim 1, wherein the membrane has a selectivity for carbon dioxide over hydrogen of at least about 5.

3. The process of claim 1, wherein the carbon dioxide-containing gas is passed across the feed side at a temperature within the range of about 0° C. to about 80° C.

4. The process of claim 1, wherein the feed side is maintained at a pressure within the range of about 3 bar to about 30 bar.

5. The process of claim 1, wherein the permeate side is maintained at a pressure within the range of about 50 bar to about 100 bar.

6. The process of claim 1, wherein the sweep stream is passed across the permeate side in a counter-current direction to the feed stream.

7. A methanol synthesis loop production process comprising the following steps:
    (a) providing a source of syngas, wherein the syngas has a composition parameter $R_1$, where $R_1>2$;
    (b) performing a methanol synthesis reaction to react the syngas to produce methanol;
    (c) performing a condensation step to recover methanol;
    (d) withdrawing a purge stream of composition parameter $R_3$ from the condensation step to limit the concentration of inerts and excess hydrogen;
    (e) withdrawing non-condensed methanol synthesis loop syngas from the condensation step;
    (f) performing a first membrane separation step comprising,
        (i) providing a first membrane having a first feed side and a first permeate side, where the first membrane exhibits a selectivity to hydrogen over carbon dioxide and carbon monoxide,
        (ii) passing at least a portion of the purge stream across the first feed side, (iii) withdrawing from the first permeate side a hydrogen-enriched first permeate stream, wherein the first permeate stream has a composition parameter $R_4$, where $R_4 > R_3$, and
(iv) withdrawing from the first feed side a hydrogen-depleted first residue stream;
(g) performing a second, sweep-based membrane separation step comprising,
(i) providing a second membrane having a second feed side and a second permeate side, where the second membrane is selective for carbon dioxide over hydrogen and methane,
(ii) passing at least a portion of the first residue stream across the second feed side,
(iii) passing at least a portion of the methanol synthesis loop syngas as a sweep stream across the second permeate side,
(iv) withdrawing from the second feed side a carbon dioxide-depleted second residue stream;
(v) withdrawing from the second permeate side a carbon dioxide-enriched second permeate stream, wherein the second permeate stream has a composition parameter $R_5$, where $R_5 < R_3$;
(h) compressing the second permeate stream; and
(i) passing the compressed second permeate stream to the methanol synthesis reaction.

8. The process of claim 7, wherein the first membrane exhibits a selectivity to hydrogen over carbon dioxide of at least about 5.

9. The process of claim 8, wherein the first membrane exhibits a selectivity to hydrogen over carbon dioxide of at least about 10.

10. The process of claim 7, wherein the first membrane exhibits a selectivity to hydrogen over carbon monoxide of at least about 20.

11. The process of claim 7, wherein the at least a portion of the purge stream is passed across the first feed side at a temperature within the range of about 50° C. to about 150° C.

12. The process of claim 7, wherein the first feed side is maintained at a pressure within the range of about 45 bar to about 100 bar.

13. The process of claim 7, wherein the first permeate side is maintained at a pressure within the range of about 2 bar to about 10 bar.

14. The process of claim 7, wherein the second membrane has a selectivity for carbon dioxide over hydrogen of at least about 5.

15. The process of claim 7, wherein the at least a portion of the first residue stream is passed across the second feed side at a temperature within the range of about 50° C. to about 150° C.

16. The process of claim 7, wherein the second feed side is maintained at a pressure within the range of about 3 bar to about 10 bar.

17. The process of claim 7, wherein the second permeate side is maintained at a pressure within the range of about 50 bar to about 100 bar.

18. The process of claim 7, wherein the sweep stream is passed across the second permeate side in a counter-current direction to the feed stream.

* * * * *